US008523020B2

(12) United States Patent
Abfall et al.

(10) Patent No.: US 8,523,020 B2

(45) Date of Patent: Sep. 3, 2013

(54) VENTED DISPENSING DEVICE

(75) Inventors: Tony J Abfall, Mount Prospect, IL (US); Kara Lineal, Northbrook, IL (US); Paul Holbrook, Buffalo Grove, IL (US)

(73) Assignee: Digital Innovations LLC, Arlington Heights, IL (US)

( * ) Notice: Subject to any disclaimer, the term of this patent is extended or adjusted under 35 U.S.C. 154(b) by 848 days.

(21) Appl. No.: 12/712,569

(22) Filed: Feb. 25, 2010

(65) Prior Publication Data

US 2010/0213276 A1 Aug. 26, 2010

Related U.S. Application Data

(60) Provisional application No. 61/155,432, filed on Feb. 25, 2009.

(51) Int. Cl.

| | |
|---|---|
| ***B67D 1/07*** | (2006.01) |
| ***B67D 7/06*** | (2010.01) |
| ***B67D 7/84*** | (2010.01) |
| ***A24F 25/00*** | (2006.01) |
| ***A61L 9/04*** | (2006.01) |

(52) U.S. Cl.

USPC ........ 222/192; 222/173; 222/179.5; 222/182; 239/34; 239/53; 239/57

(58) Field of Classification Search

USPC ..... 239/34, 53, 55, 57, 58, 59, 145; 222/173, 222/179.5, 182, 183, 192

See application file for complete search history.

(56) References Cited

U.S. PATENT DOCUMENTS

| | | | | |
|---|---|---|---|---|
| 1,202,642 | A | 10/1916 | Allen | |
| 1,255,772 | A | 2/1918 | Miller | |
| 1,280,541 | A | 10/1918 | Potthoff | |
| 1,355,482 | A | 10/1920 | Lees | |
| 1,523,297 | A | 1/1925 | Savery | |
| 1,582,645 | A | 4/1926 | Findley | |
| 1,615,319 | A | 1/1927 | Wynn | |
| 1,657,050 | A | 1/1928 | Walter | |
| 1,879,517 | A | 9/1932 | Robotham | |
| 1,942,953 | A | 1/1934 | Bennett | |
| 2,292,413 | A | 8/1942 | Taylor | |
| 2,401,318 | A | 6/1946 | Robinson et al. | |
| 2,438,129 | A | 3/1948 | Rich | |
| 2,620,085 | A | 12/1952 | Baldanza | |
| 2,657,090 | A | 10/1953 | Meek | |
| 2,765,194 | A | 10/1956 | Will | |
| 2,769,565 | A | 11/1956 | Sottile | |
| 2,783,084 | A | 2/1957 | Paxton | |
| 2,864,118 | A | 12/1958 | Adams et al. | |
| 2,935,186 | A | 5/1960 | Clark | |
| 3,330,481 | A * | 7/1967 | Dearling | 239/47 |
| 3,508,559 | A | 4/1970 | Wolfe | |
| 3,662,913 | A | 5/1972 | Mascia | |
| 3,746,158 | A | 7/1973 | Connick | |
| 3,763,998 | A | 10/1973 | Fisher | |
| 3,768,688 | A | 10/1973 | Linke | |
| 3,848,803 | A | 11/1974 | Levey | |
| 3,972,473 | A * | 8/1976 | Harrison | 239/34 |

(Continued)

*Primary Examiner* — Ryan Reis

(74) *Attorney, Agent, or Firm* — Clifford Kraft

(57) ABSTRACT

The dispensing device provides dispensable material in a closable container in concert with a corresponding accessory so that the container and the accessory can be commonly stored when not in use, and further provides a ventilated storage volume within the device that can facilitate drying and aerating the accessory.

11 Claims, 8 Drawing Sheets

(56) References Cited

U.S. PATENT DOCUMENTS

| | | | | |
|---|---|---|---|---|
| 4,084,732 | A * | 4/1978 | Dearling | 222/402.17 |
| 4,200,229 | A * | 4/1980 | Spector | 239/57 |
| 4,341,348 | A * | 7/1982 | Dearling | 239/34 |
| 4,436,224 | A | 3/1984 | McInerny | |
| 4,516,676 | A | 5/1985 | Cournoyer | |
| 4,522,298 | A | 6/1985 | Weinberger | |
| 4,726,519 | A * | 2/1988 | Muoio | 239/49 |
| 4,759,501 | A * | 7/1988 | Silvenis et al. | 239/6 |
| 4,818,134 | A | 4/1989 | Tsai | |
| 4,927,284 | A | 5/1990 | Tsai | |
| 4,953,999 | A | 9/1990 | Rivers | |
| 4,974,727 | A | 12/1990 | Karasin et al. | |
| 5,100,010 | A | 3/1992 | Waters | |
| 5,769,263 | A | 6/1998 | Willingham et al. | |
| 6,000,580 | A | 12/1999 | Nilson | |
| 6,029,901 | A | 2/2000 | Toy, II | |
| 6,170,651 | B1 | 1/2001 | Taormina | |
| 6,321,937 | B1 | 11/2001 | DeSimone et al. | |
| 6,536,977 | B1 | 3/2003 | Hammel | |
| 6,883,989 | B2 | 4/2005 | Kushner et al. | |
| 7,074,443 | B2 | 7/2006 | Thomas et al. | |
| 7,225,950 | B2 | 6/2007 | McKay | |
| 7,370,754 | B2 | 5/2008 | Kushner | |
| 7,465,116 | B2 | 12/2008 | Sorrell | |
| 7,585,125 | B2 | 9/2009 | Muhlhausen et al. | |
| 7,743,947 | B2 | 6/2010 | Flasch | |
| D630,010 | S | 1/2011 | Brown | |
| 2007/0067934 | A1 | 3/2007 | Osborne | |
| 2009/0032553 | A1 | 2/2009 | Eddy | |
| 2011/0000977 | A1 | 1/2011 | Withers | |

* cited by examiner

VENTED DISPENSING DEVICE

This application claims the priority of provisional application 61/155,432 filed Feb. 25, 2009 which is incorporated in full herein by reference.

The vented dispensing device can provide dispensable material in a closable container in concert with a suitable applicator so that the container and the applicator can be cooperatively stored when not in use. The dispensing device can further provide a ventilated storage volume within the device that can facilitate drying the applicator, for example when the dispensed container contents comprise liquids, and for aerating the applicator, for example to minimize mold growth and other unwanted conditions that can be minimized by air flow. Other benefits can be realized by the ventilated storage volume configuration beyond the aforementioned, including but not limited to dispersing fragrance and masking environmental odor.

SUMMARY OF THE INVENTION

In one embodiment, the vented dispensing device can comprise a dispensing accessory and a container. The container can comprise a dispensing nozzle for dispensing container contents, and a vented cover for retaining the dispensing accessory proximal to the container. The vented cover in use can connect to the container and can define an accessory storage volume between the vented cover and the container. The vented cover can have a vent opening extending through the vented cover to ventilate the storage volume; and at least part of the dispensing accessory can be confined within the storage volume when the vented cover is in use.

In another embodiment, the vented dispensing device can comprise a dispensing accessory and a container. The container can comprise a dispensing nozzle for dispensing container contents. The dispensing nozzle can have a trigger and a trigger cap, where the trigger cap can be connected to the container and spaced apart from the trigger. The trigger cap in use can limit contact between the dispensing accessory and the trigger. The container can further comprise a vented cover for retaining the dispensing accessory proximal to the container. The vented cover in use can connect to the container and can define an accessory storage volume between the vented cover and the container. The vented cover can have at least one vent opening extending through the vented cover to ventilate the storage volume, and at least part of the dispensing accessory can be confined within the storage volume when the vented cover is in use.

In another embodiment, the vented dispensing device can comprise a dispensing accessory and a container. The container can comprise a nozzle end, a reservoir end, and a trunk connecting the nozzle end and the reservoir end. The container can further comprise a dispensing nozzle connected to the nozzle end, the nozzle for dispensing container contents. The nozzle can comprise a trigger, with the trigger being movable to release container contents through the nozzle. The container can further comprise a trigger guard extending along a trigger perimeter, the trigger guard limiting access to the trigger across the perimeter. The container can further comprise a vented cover in use retaining the dispensing accessory proximal to the container. The vented cover can comprise an open end and vent end. The open end can be configured to receive the trunk, the nozzle end, and the nozzle, and to connect to the container proximal to the reservoir end. The vent end can comprise a plurality of vent openings through the vented cover, the vent openings positioned to facilitate airflow around the nozzle when the vented cover is in use. The vented cover in use can connect to the container to define an accessory storage volume between the vented cover and the container, and at least part of the dispensing accessory can be confined in the storage volume when the vented cover is in use.

FIGURES

DETAILED DESCRIPTION

Figure 1:
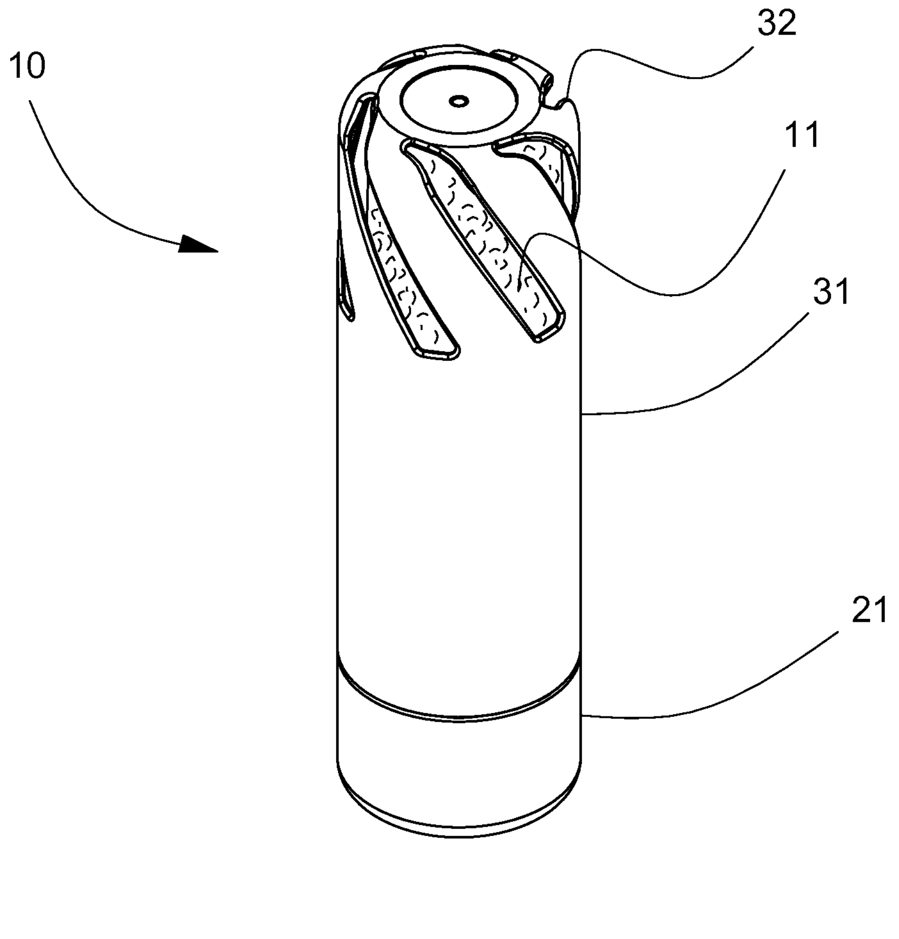
FIG. 1 is an isometric view of an embodiment of the dispensing device.

The vented dispensing device can comprise a dispensing accessory and a container. The container can hold dispensable material such as cleaning fluid, finishes like polish and wax, powder, compressed air and other gases, and various other materials and combinations thereof.

The container can comprise various geometric and organic shapes. The container can be cylindrical, prismatic, cone-shaped, and various shapes and combinations thereof.

The container can be configured with engagement features, for example, depressions, protrusions, hooks, forks, and various other features and combinations thereof.

The container can further comprise a plurality of content sections, for example, separate sections for holding different contents.

The container can comprise a nozzle end, a reservoir end, and a trunk connecting the nozzle end and the reservoir end. The container can be open at the nozzle end, and can have various other openings.

The dispensing accessory can be utilized to apply container contents, can be utilized to remove dispensed container contents, for example excess material, overspray, and used cleaning fluid, can be used to buff, polish, shine, and otherwise affect finish.

The dispensing accessory can be a towel, a soft pad, a sponge, and various other accessories and combinations thereof. The dispensing accessory can be a brush, a cotton ball, and a swab.

The container can comprise a dispensing nozzle for dispensing container contents. The dispensing nozzle can selectively open and close the container. The dispensing nozzle can close the container at the nozzle end.

The dispensing nozzle can comprise a pump, a valve, a hinged flap, and various dispensing mechanisms and combinations thereof. The dispensing nozzle can comprise an opening such as an orifice, an aperture, and an elongate tube. The dispensing nozzle can comprise a plurality of openings. The dispensing nozzle can have an open position and a closed position. The dispensing nozzle can have a plurality of open positions, for example, when utilized with a container having a plurality of content sections, the open positions from the plurality of open positions can correlate to respective container content sections.

The container can further comprise a vented cover. The vented cover can facilitate retaining the dispensing accessory proximal to the container. The vented cover in use can connect to the container and define an accessory storage volume between the vented cover and the container.

The vented cover can receive at least part of the container within the vented cover. For example, the vented cover can be configured to enclose the container including the nozzle within the storage volume. Alternatively, the vented cover can enclose the vented cover except for the nozzle within the storage volume. Alternatively, the vented cover can be configured to enclose the nozzle in one position, and to enclose the container except for the nozzle in another position. Alternatively, the vented cover can connect to the container and not receive a part of the container within the vented cover.

The vented cover can comprise a vent opening extending through the vented cover. The vent opening can facilitate air flow into and out of the accessory storage volume to ventilate the accessory storage volume.

The vent opening can be positioned on the vented cover to ventilate a predetermined part of the storage volume, for example, to ventilate the storage volume proximal to the nozzle. Similarly, other parts of the storage volume where moisture is likely to collect can be targeted by positioning the vent opening to ventilate the predetermined part of the storage volume. The vented cover can comprise an open end and a nozzle end and can be configured to receive the container including the nozzle through the open end so that the nozzle is positioned proximal the nozzle end when the vented cover is in use.

The vented cover, in use connected to the container, can confine at least part of the dispensing accessory within the accessory storage volume. Confining part of the dispensing accessory within the accessory storage volume can facilitate retaining the dispensing accessory proximal to the container when the dispensing accessory is not in use.

When the vented cover is in use and part of the dispensing accessory is confined within the accessory storage volume, the vent opening can facilitate drying the accessory and can prevent accumulation of excess container content on the accessory and within the storage volume.

The vented cover can comprise a plurality of vent openings. The plurality of vent openings can be positioned on the vented cover so that each vent opening ventilates one or more predetermined parts of the storage volume.

The vented cover can be configured to define a plurality of accessory storage volumes between the vented cover and the container, when the vented cover is in use. The vented cover can confine at least parts of dispensing accessories from a plurality of dispensing accessories within the plurality of accessory storage volumes.

The container can comprise a plurality of vented covers and each cover from the plurality of vented covers can connect to the container directly and can connect to the container via connecting to another cover from the plurality of vented covers.

Figure 2:
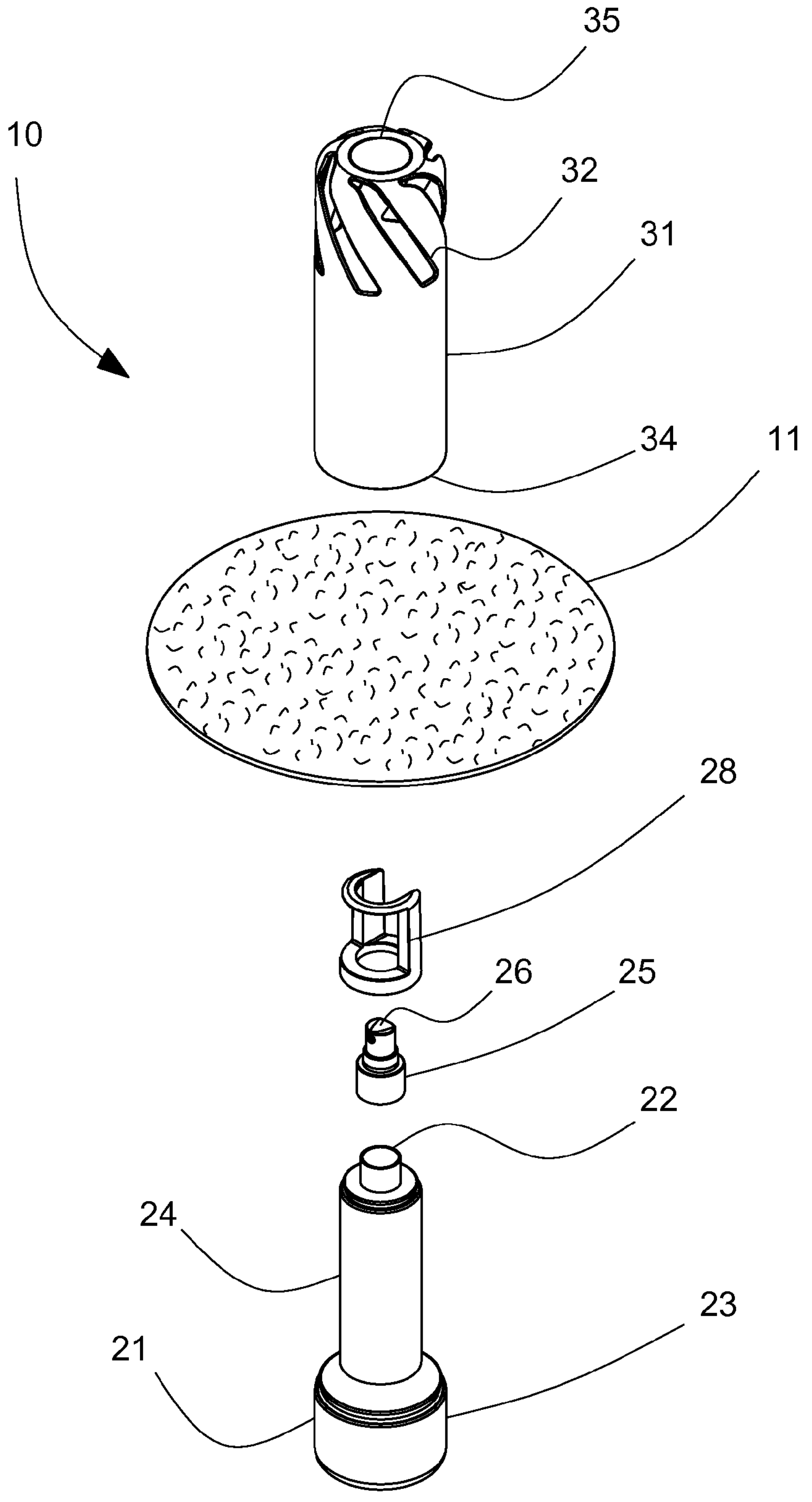
FIG. 2 is an exploded view of the above embodiment.
Figure 3:
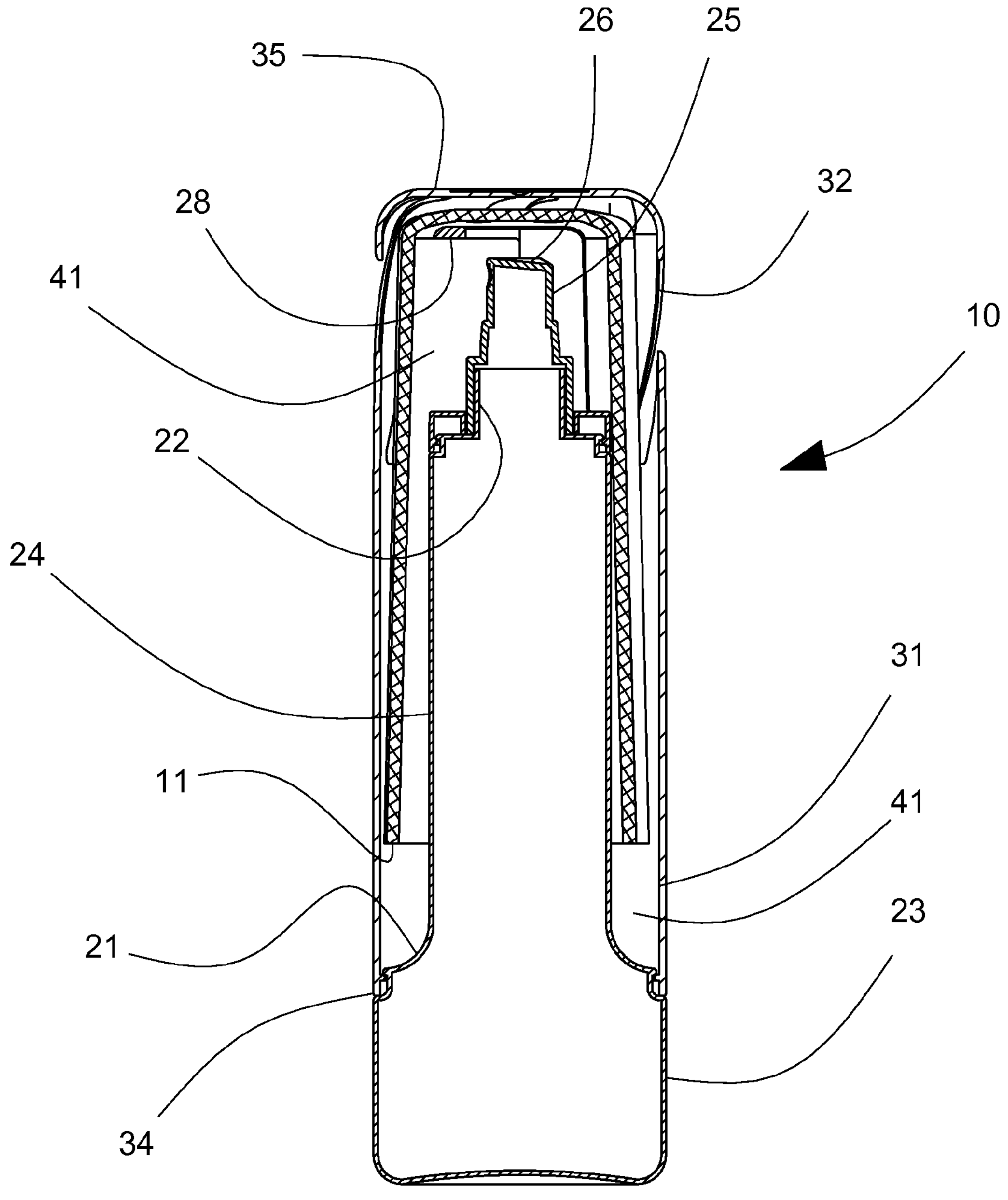
FIG. 3 is a side section view of the above embodiment.

In the embodiment of FIGS. 1, 2, and 3, the dispensing device 10 comprises a dispensing accessory 11, a container 21, a dispensing nozzle 25, and a vented cover 31.

The dispensing accessory 11 comprises a cloth-like accessory for applying, distributing, and removing dispensed container contents.

The container 21 comprises a generally cylindrically-shaped trunk 24 with a reduced neck at the nozzle end 22 and a larger cylindrically-shaped reservoir end 23. The nozzle 25 closes the container 21 at the nozzle end 22.

The vented cover 31 connects to the container 21 and defines an accessory storage volume 41 between the vented cover 31 and the container 21. In use, the vented cover 31 receives the container 21 through the vented cover open end 34 and connects to the container 21 proximal the container reservoir end 23. The vented cover 31 encloses the nozzle 25 within the accessory storage volume 41.

The vented cover 31 comprises a plurality of vent openings, such as the vent opening 32. The vent opening 32 extends through the vented cover 31 and enables air to flow through the vented cover 31 and facilitates ventilating the storage volume 41. In use connected to the container 21, the vent opening 32 is positioned at the vent end 35 to ventilate the storage volume 41 proximal to the nozzle 25.

As shown explicitly in FIGS. 1 and 3, the dispensing accessory 11 is confined within the storage volume 41 when the vented cover 21 is in use. The cloth-like accessory 11 can drape over the nozzle 25 and extend along the container trunk 24. With the vented cover 31 in use connected to the container 21, the dispensing accessory 11 is substantially confined within the accessory storage volume 41 between the vented cover 31 and the container 21.

Additionally, when the dispensing accessory 11 is confined within the storage volume 41 as shown in FIGS. 1 and 3, the vent opening 32 is positioned to ventilate the middle part of the dispensing accessory 11. Observations of common usage have shown that the middle part of the cloth-like accessory 11 can accumulate excess container contents and so benefits from maximum ventilation.

The nozzle can comprise a trigger for causing the nozzle to dispense container contents. The trigger can be movable to release container contents through the nozzle. The trigger can activate another component to cause release of container contents. The trigger can cause dispensing via various means and methods.

The trigger can comprise a spray head with a finger-positioning depression, a lever for pumping container contents from the container through the nozzle, a valve release actuator, and a pushbutton. The trigger can comprise various other mechanisms and indicators and combinations thereof, which facilitate dispensing container contents via the nozzle.

The nozzle 25 of the container 21 comprises a trigger 26. The trigger 26 is movable to release container contents, for example, to release pressurized gases.

The container can further comprise a trigger cap. The trigger cap can prevent unintentional trigger movement and can prevent accidental dispensing of the container contents. The trigger cap can be positioned proximal to the trigger and can limit contact between the dispensing accessory and the trigger, especially when the dispensing accessory is confined within the storage volume.

The trigger cap can enclose the trigger and can enclose the nozzle. Alternatively, the trigger cap can extend adjacent to the trigger to limit contact between the dispensing accessory and the trigger.

The trigger cap can comprise a trigger guard extending along a trigger perimeter, where the trigger perimeter at least party encircles the trigger. The trigger guard can limit access to the trigger across the perimeter and enable access to the trigger from other directions. The trigger guard can provide similar protection as the trigger cap against accidental discharge while still enabling selective access to the trigger while the trigger guard is in use.

Figure 4:
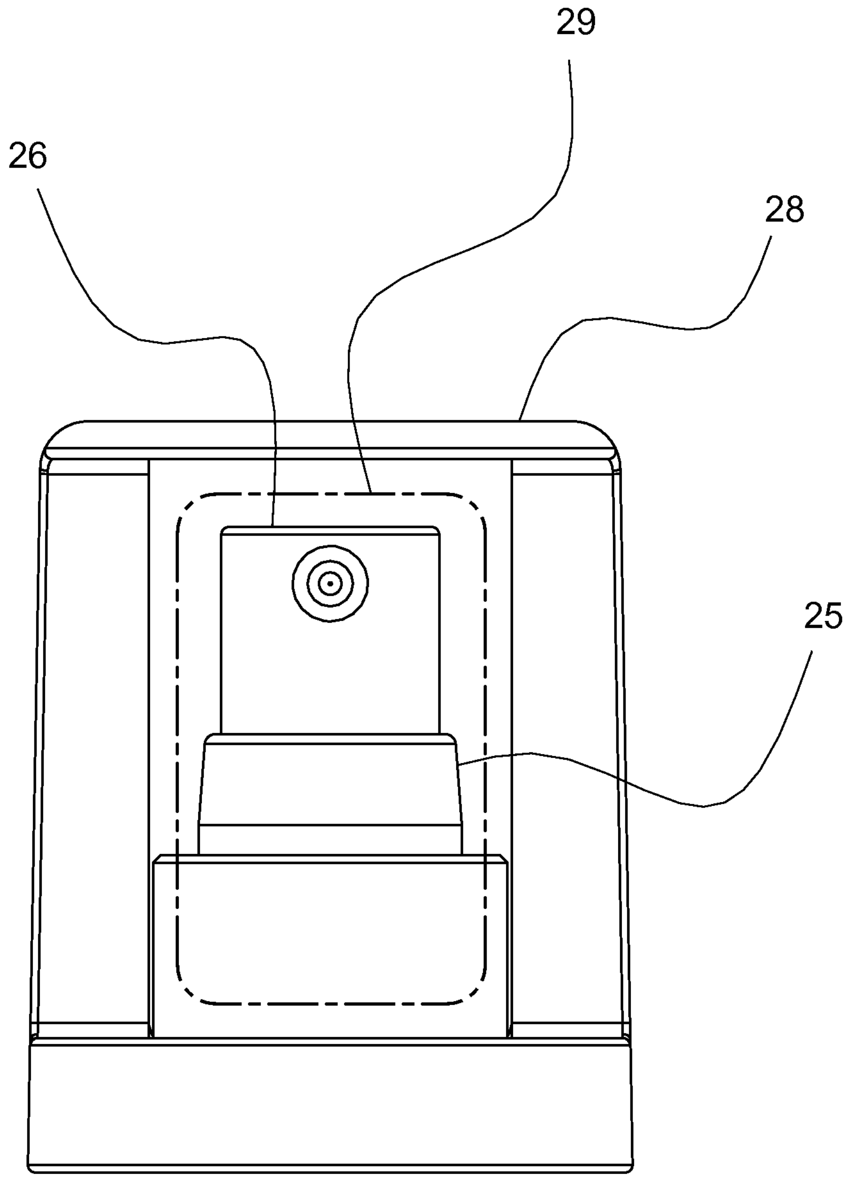
FIG. 4 is a front view of an embodiment of a dispensing nozzle with a trigger guard showing a trigger perimeter.

As shown in FIGS. 2, 3, and 4, the container 21 includes a trigger cap comprising a trigger guard 28. The trigger guard 28 extends over the trigger 26 along a trigger perimeter 29, and limits access to the trigger 26 across the trigger perimeter 29. With the trigger guard 28 in use, access to the trigger 26 is enabled through (but not across) the trigger perimeter 29. When the dispensing accessory 11 is confined within the storage volume 41, the dispensing accessory 11 can be spaced apart from the trigger 26 by the trigger guard 28 to prevent accidental discharge of container contents.

Figure 5:
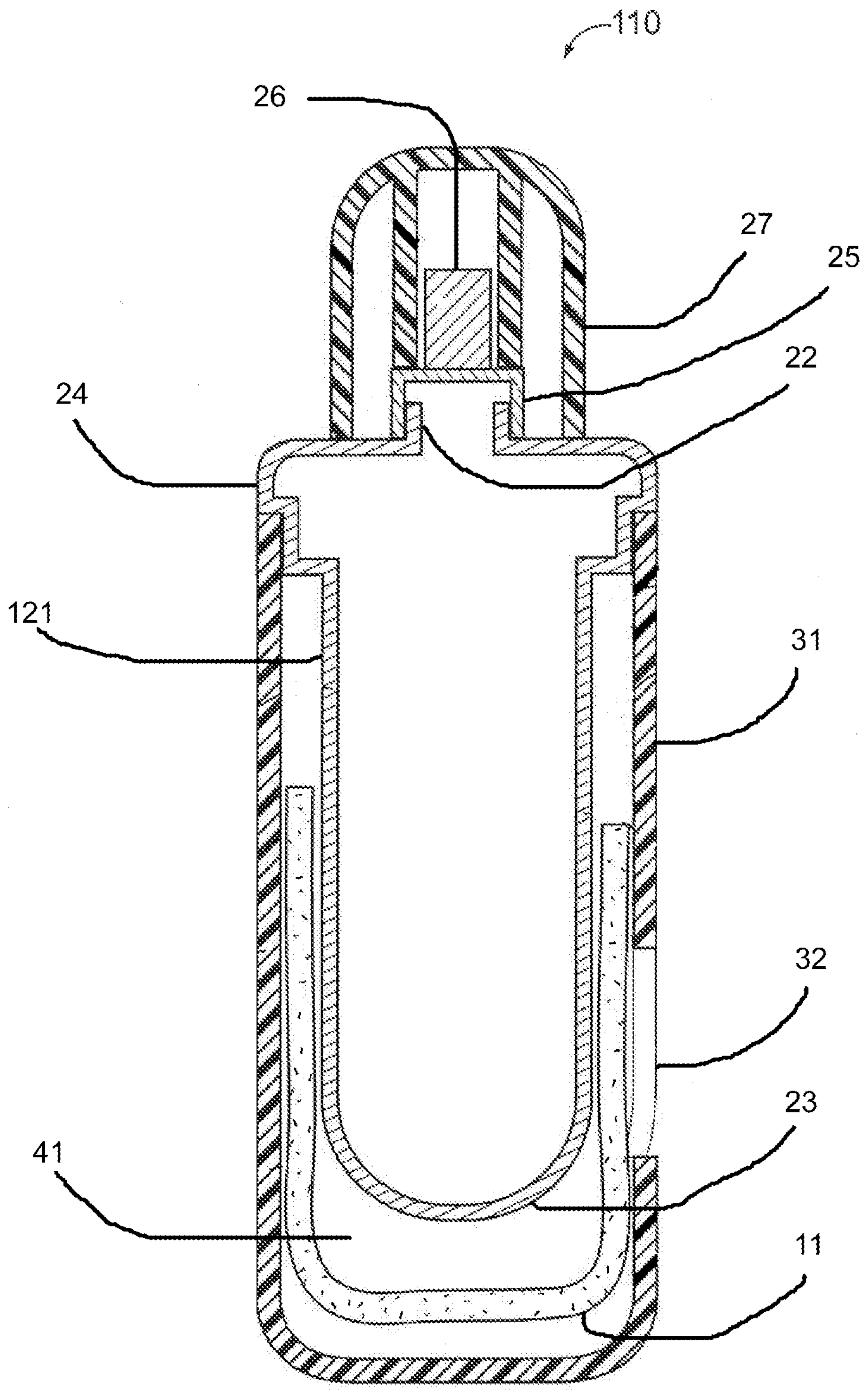
FIG. 5 is a side section view of another embodiment

In the embodiment shown in FIG. 5, the dispensing device 110 comprises a container 121. The container 121 is generally cylindrically-shaped including a reduced neck at the nozzle end 22 and a larger trunk 24 connecting the nozzle end 22 and the reservoir end 23.

The container 121 comprises a nozzle 25 with a trigger 26, where the nozzle 25 closes the container 121 at the nozzle end 22. The container 121 further comprises a trigger cap 27. The trigger cap 27 in use fully covers the trigger 26 to prevent accidental discharge.

The vented cover 31 of the dispensing device 110 connects to the container 121 proximal the trunk 24, enclosing the reservoir end 23 and not enclosing the nozzle 22 and the trigger cap 27. The dispensing accessory 11 is confined within the accessory storage volume 41 when the vented cover 31 is in use. The vented cover 31 comprises a plurality of vent openings, such as the vent opening 32, and the vent opening 32 is positioned on the vent cover 31 so that the storage volume 41 is ventilated proximal to the dispensing accessory 11.

Figure 6:
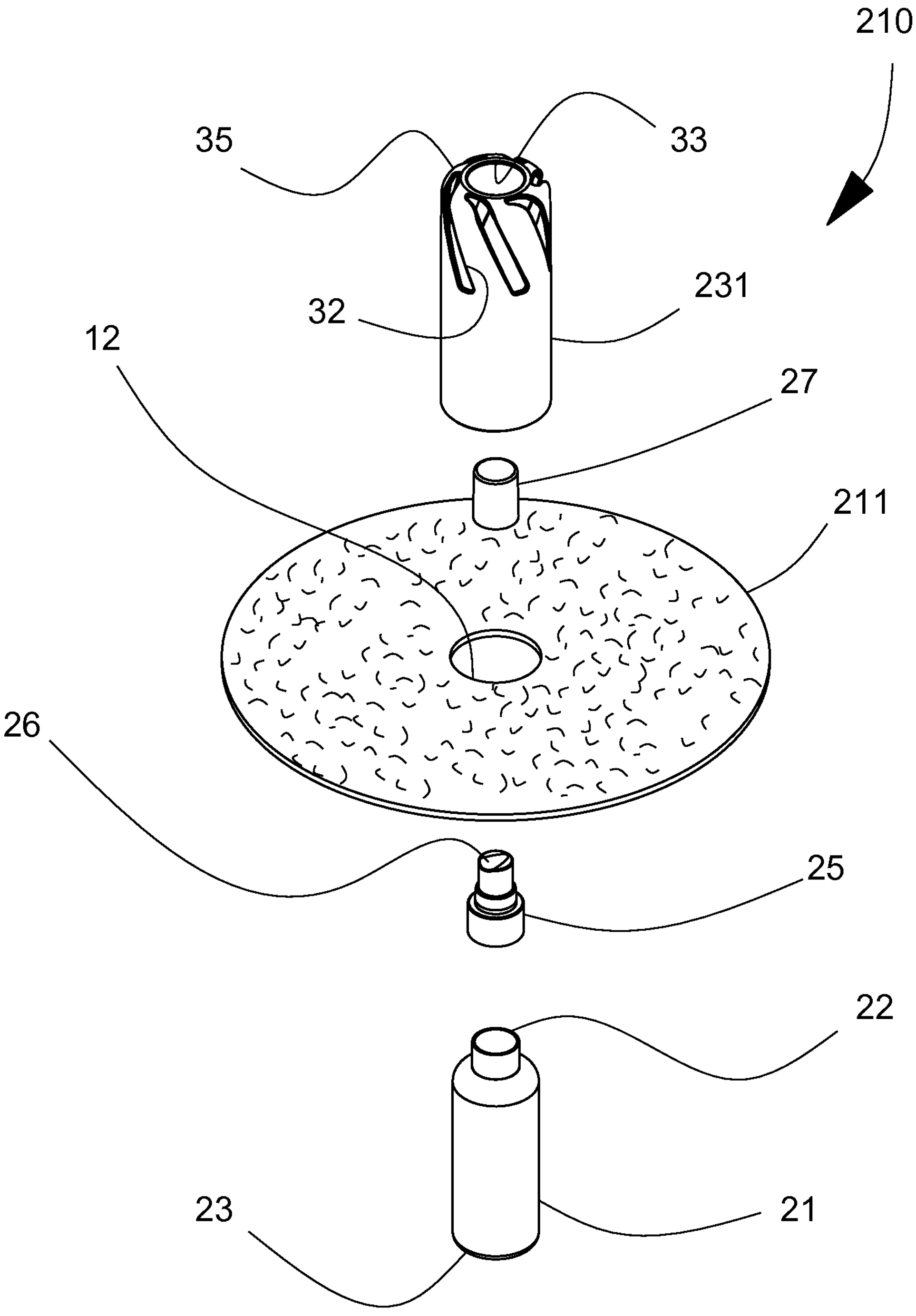
FIG. 6 is an exploded view of another embodiment including a trigger cap, a cover nozzle opening and an accessory nozzle opening.
Figure 7:
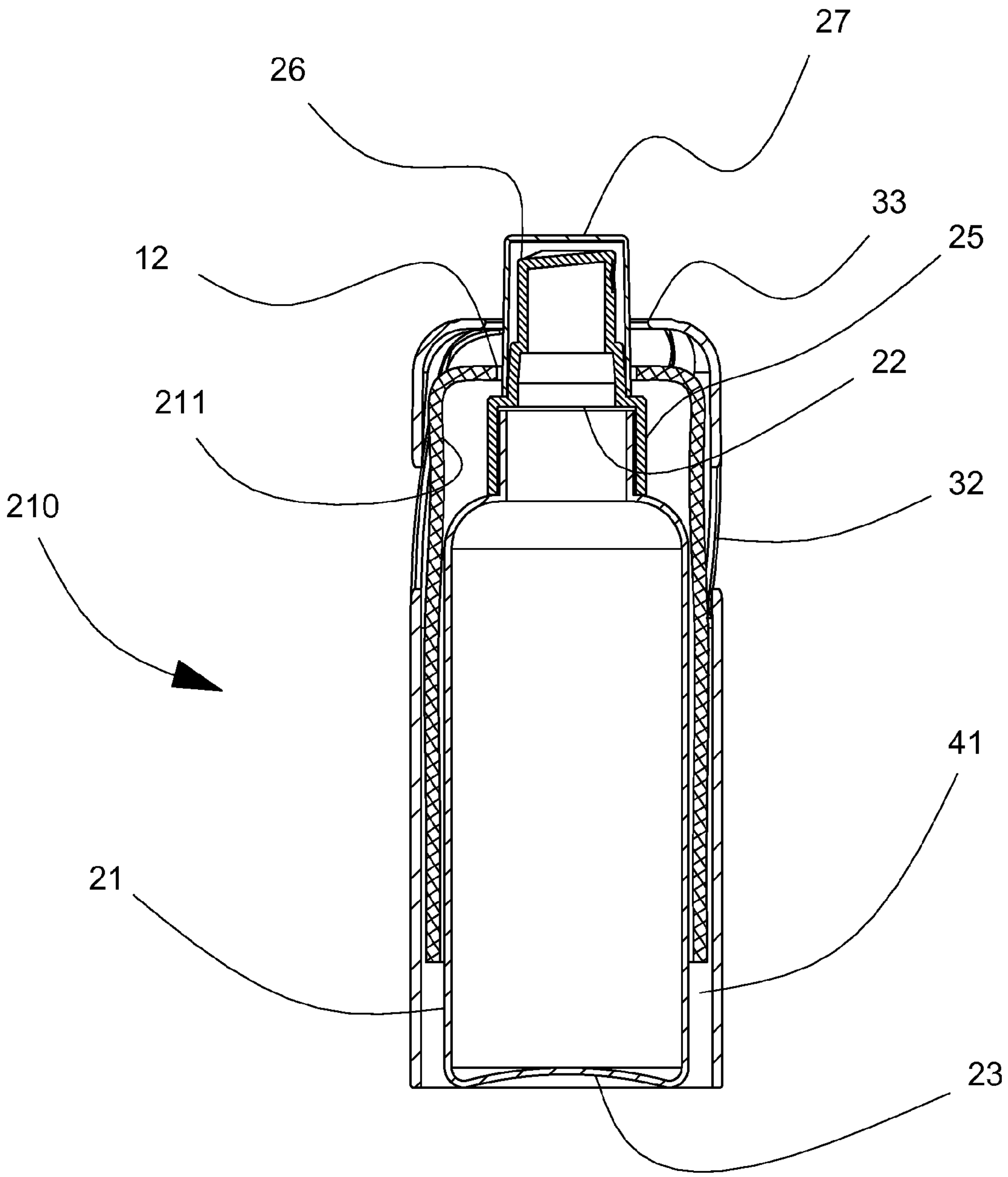
FIG. 7 is a side section view of the above embodiment.

In the embodiment shown in FIGS. 6 and 7, the dispensing device 210 comprises a container 21, a dispensing accessory 211, and a vented cover 231. The dispensing accessory 211 further comprises an accessory nozzle opening 12 through the middle part of the dispensing accessory 211. The vented cover 231 further comprises a cover nozzle opening 33 through the vent end 35 of the vented cover 231.

The container 21 comprises a nozzle 25 with a trigger 26, where the nozzle 25 closes the container 21 at the nozzle end 22. The container 21 further comprises a trigger cap 27. The trigger cap 27 in use fully covers the trigger 26 to prevent accidental discharge.

The vented cover 231 connects to the container 21 and defines an accessory storage volume 41 between the vented cover 231 and the container 21. In use, the vented cover 331 receives the container 21 through the vented cover open end 34 and connects to the container 21 proximal the reservoir end 23. The vented cover 31 encloses the container 21 and not the nozzle 25 within the accessory storage volume 41.

When the vented cover 31 is in use, the nozzle 25 and the trigger cap 27 protrude through the accessory nozzle opening 12 and through the cover nozzle opening 33 so that the nozzle 25 and the trigger cap 27 are accessible when the vented cover 231 is in use.

Figure 8:
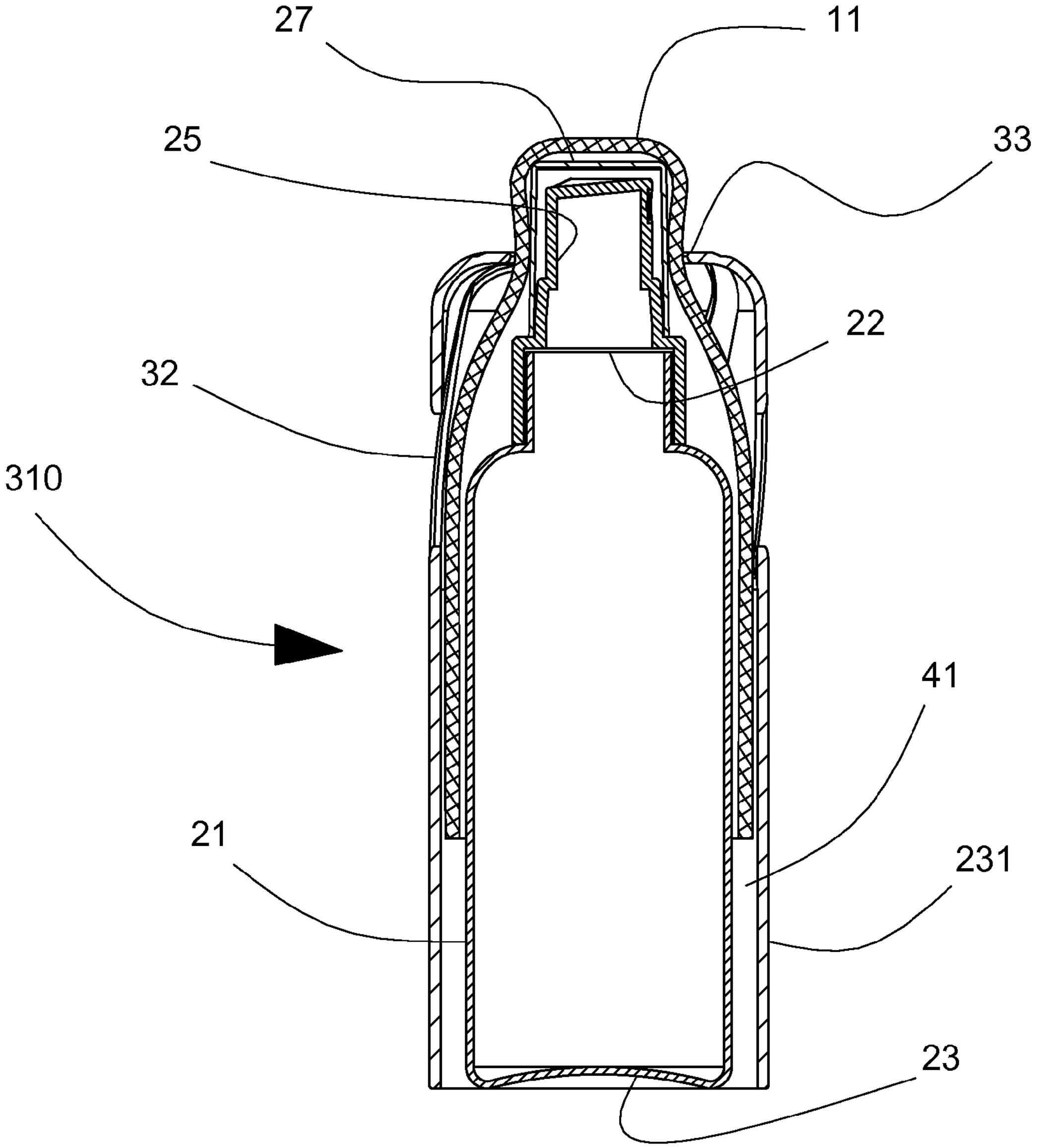
FIG. 8 is a side section view of another embodiment.

In the embodiment shown in FIG. 8, the dispensing device 310 comprises a vent cover 231 having a cover nozzle opening 33 and a dispensing accessory 11 with no accessory nozzle opening. When the vented cover 231 is in use, the nozzle 25 and the trigger cap 27 protrude through the cover nozzle opening 33 but are covered by the dispensing accessory 11. The dispensing accessory 11 drapes over the nozzle 25 and the trigger cap 27 and passes into the accessory storage volume 41 through the cover nozzle opening 33 to be confined within the storage volume 41.

The invention claimed is:

1. A method of storing a wipe in a dispenser container cover comprising:

utilizing a dispensing container that dispenses a cleaning liquid;

utilizing a removable cover adapted to fit over said dispensing container; utilizing a space between said cover and said dispensing container to receive said wipe in a storage configuration, whereby said wipe receives air circulation from at least one vent in said removable cover allowing said wipe to dry;

independently removing said wipe from said space by removing said cover, wherein said wipe receives a portion of said cleaning liquid becoming damp and is used for cleaning a surface;

allowing said damp wipe to be returned to said dispensing container and stored by closing said cover, wherein said wipe dries in said cover.

2. The method of claim 1 wherein said cover contains a plurality of vents.

3. The method of claim 2 wherein the vents are elongated.

4. The method of claim 1 wherein said container has a dispensing nozzle.

5. A method of utilizing a towel with a dispensing container and allowing the towel to dry when not in use comprising:

utilizing a liquid dispensing container and cover to receive and store said towel draped over the container by utilizing a towel storage space between the container and the cover;

utilizing said cover to allow air circulation through the towel by utilizing at least one slot in the cover so that said towel can dry;

removing said towel by removing the cover, wetting said towel with said liquid from said dispensing container and cleaning a surface;

permitting said towel to be repositioned in said towel storage space by draping the towel over the container and replacing the cover;

allowing said towel to dry in said storage space.

6. The method of claim 5 wherein said slot is elongated.

7. The method of claim 5 wherein said dispensing container includes a dispensing nozzle.

8. The method of claim 7 wherein said dispensing nozzle is connected to a dispensing pump.

9. The method of claim 7 wherein said dispensing nozzle includes a trigger movable to release contents of the container through said dispensing nozzle.

10. The method of claim 5 wherein said dispensing container dispenses a liquid under pressure.

11. The method of claim 5 wherein said towel is round.

* * * * *